United States Patent [19]

Wang

[11] Patent Number: 5,408,326
[45] Date of Patent: Apr. 18, 1995

[54] DUAL-WAVELENGTH ABSORPTION DETECTOR ADAPTED FOR CONTINUOUS-FLOW DETECTION

[75] Inventor: Priestley J. Wang, Houston, Tex.
[73] Assignee: Shell Oil Company, Houston, Tex.
[21] Appl. No.: 53,784
[22] Filed: Apr. 28, 1993
[51] Int. Cl.$^6$ ............................................. G01N 21/85
[52] U.S. Cl. .................................. 356/410; 250/576; 354/440
[58] Field of Search ............... 356/410, 411, 402, 425, 356/436, 440; 250/573, 576

[56] References Cited

U.S. PATENT DOCUMENTS

| | | | |
|---|---|---|---|
| 2,980,512 | 4/1961 | Petersen | 23/253 |
| 3,327,584 | 6/1967 | Kissinger | 88/14 |
| 3,592,607 | 7/1971 | Bruce | 23/253 |
| 3,666,941 | 5/1970 | Watson . | |
| 3,807,875 | 4/1974 | Fischer et al. . | |
| 3,910,701 | 10/1975 | Henderson et al. | 356/39 |
| 3,967,902 | 7/1976 | Steinberg . | |
| 4,000,990 | 1/1977 | Bingham . | |
| 4,188,126 | 12/1980 | Boisde et al. . | |
| 4,276,475 | 6/1981 | Nelson . | |
| 4,281,387 | 7/1981 | Kraft et al. . | |
| 4,321,930 | 3/1982 | Jobsis et al. . | |
| 4,473,296 | 9/1984 | Shofner et al. . | |
| 4,475,813 | 10/1984 | Munk . | |
| 4,565,447 | 1/1986 | Nelson . | |
| 4,600,310 | 7/1986 | Cramp et al. . | |
| 4,628,463 | 12/1986 | Sturrock et al. . | |
| 4,631,529 | 12/1986 | Zeitz . | |
| 4,637,729 | 1/1987 | Schoch | 356/408 |
| 4,678,338 | 7/1987 | Kitta et al. | 356/420 |
| 4,688,017 | 8/1987 | Huebner et al. . | |
| 4,747,687 | 5/1988 | Hoppe et al. . | |
| 4,775,794 | 10/1988 | Behmann . | |
| 4,784,494 | 11/1988 | Pawliszyn . | |

(List continued on next page.)

OTHER PUBLICATIONS

P. K. Dasgupta et al "Light Emitting Diode Based Flow Through Optical Absorption Detectors." Shell Oil Co., Nov. 15, 1991, *Talanta*, vol. 40 pp. 53-74 (1993).

J. Huang et al "A Dual Wavelength Light Emitting Diode Based Detector for Flow Injection Analyzers" *Talanta*, vol. 39 No. 6 pp. 589-592 (1992).

P. K. Dasgupta et al., "Light Emitting Diode Based Flow-Through Optical Absorption Detectors." Shell (List continued on next page.)

Primary Examiner—Vincent P. McGraw
Assistant Examiner—Russell C. Wolfe
Attorney, Agent, or Firm—Fred S. Reynolds

[57] ABSTRACT

A dual-wavelength absorption detector is provided. The detector includes an electronics section, a three branched optical guide and a detector-cell. Each branch of the optical guide has a plurality of fibers, and at one end the branches are separated and connected to different portions of the electronics section. Two of the three branches are terminated next to LEDs having different wavelengths, a measuring wavelength and a reference wavelength. The third branch is terminated next to a photodetector. At the opposite end of the optical guide the three branches are combined to form a common end which is terminated within the detector-cell. The detector-cell includes a continuous-flow sample cell connected to a sample line. Within the detector-cell, the common end's fiber ends are held at a fixed location on one side of the sample cell with a concave mirror being located on the opposite side. Sequential pulses of light from the LEDs are guided through their respective branches to the common end where they cross the sample cell to be absorbed by sample material flowing through the cell. Portions of each pulse are reflected by the concave mirror back across the sample cell to the common end and strike the photodetector branch fiber ends. At the photodetector, signals proportional to the illumination intensity of the pulses striking the fiber ends are produced. The signals are then compared to provide an output signal which represents the absorption of the sampled material.

26 Claims, 6 Drawing Sheets

U.S. PATENT DOCUMENTS

| | | |
|---|---|---|
| 4,804,266 | 2/1989 | Barshad . |
| 4,820,045 | 4/1989 | Boisde et al. . |
| 4,940,333 | 7/1990 | Pawliszyn . |
| 4,943,159 | 7/1990 | Oetliker et al. . |
| 4,973,561 | 11/1990 | Hansen et al. .......................... 436/52 |
| 5,001,054 | 3/1991 | Wagner . |
| 5,015,843 | 5/1991 | Seitz et al. ...................... 250/227.21 |
| 5,035,505 | 7/1991 | Tsukada et al. . |
| 5,046,854 | 9/1991 | Weller et al. ........................ 356/440 |
| 5,066,097 | 11/1991 | Brandle et al. . |
| 5,073,029 | 12/1991 | Eberly et al. . |
| 5,085,499 | 2/1992 | Griffin et al. . |
| 5,119,024 | 6/1992 | Popovic et al. ...................... 356/345 |
| 5,125,747 | 6/1992 | Sayegh et al. ....................... 356/410 |
| 5,148,239 | 9/1992 | Magnussen, Jr. et al. . |
| 5,153,666 | 10/1992 | Pawliszyn . |
| 5,153,679 | 10/1992 | Gilby . |

OTHER PUBLICATIONS

Oil Company received the enclosed pre-publication copy on Nov. 15, 1991. The article was subsequently accepted for publication and published in *Talanta*, vol. 40, pp. 53–74 (1993).

*Process Instruments And Controls Handbook*, Douglas M. Considine, Editor-in-Chief, McGraw-Hill Book Company, Third Edition (1985), pp. 6.63–6.73, 6.89–6.91, and 6.169–6.187.

J. Ruzicka et al., "Flow Injection Analyses, Part I. A New Concept of Continuous Flow Analysis," *Analytica Chimica Acta.*, 78, pp. 145–157 (1975) Elsevier Scientific Publishing Co., Amsterdam.

D. Betteridge et al., "A Highly Sensitive Flow-Through Phototransducer for Unsegmented Continuous-Flow Analysis Demonstrating High-Speed Spectrophotometry at the Parts Per $10^9$ Level and a New Method of Refractometric Determinations," *The Analyst*, vol. 103, No. 1230, pp. 897–907 (Sep. 1978).

J. Huang et al., "A Dual-Wavelength Light-Emitting Diode Based Detector for Flow-Injectin Analysis Proess Analysers," *Talanta*, vol. 39, No. 6, pp. 589–592 (1992).

E. A. G. Zagatto et al., "Compensation of the Schlieren Effect in Flow-Injection Analysis by Using Dual-Wavelength Spetrophotometry," *Analytica Chimica Acta.*, 234, pp. 153–160 (1990).

V. Kuban et al., "Nitroprusside and Methylene Blue Methods for Silicone Membrane Differentiated Flow Injection Determination of Sulfide in Water and Wastewater," *Anal. Chem.*, 64, pp. 36–43 (1992).

Series 6000 Process Diode Array [brochure], Ametek Process & Analytical Instruments Division, Ametek, Inc. Newark, Delaware (1991).

Model 400 Photometric Analyzers, Bulletin P-400, Ametek Process & Analytical Instruments Division, Ameteck, Inc., Newark, Delaware (1992).

Alfa-Laval/Bran+Luebbe Market Information [brochure], Bran+Luebbe Analyzing Technologies, Elmsford, N.Y. (1992).

DUAL-WAVELENGTH ABSORPTION DETECTOR ADAPTED FOR CONTINUOUS-FLOW DETECTION

BACKGROUND OF THE INVENTION

1. Field of the Invention

This invention relates to dual-wavelength absorbance detection in chemical analysis and more particularly to dual-wavelength optical absorption detectors used in continuous flow analysis, flow injection analysis, colorimetry and liquid and gas chromatography.

2. Description of the Related Art

Developments in the techniques and methodologies of chemical analysis have advanced rapidly over the last several years, especially for laboratory instruments; however, the evolution of state-of-the-art hardware designed specifically for the measurement of absorption in continuous flow analysis, FIA (flow injection analysis), colorimetry or HPLC (high performance liquid chromatography) has lagged far behind. Currently, dual-wavelength absorption analysis is done with complex instruments that are not specifically designed for dual-wavelength absorption detection such as an expensive, bulky, bench-top spectrophotometer. Or, it is done with single beam, dual-wavelength absorption detectors which have inherent design limitations that increase the cost of sampling and/or reduce the performance of the detector.

In this specification, dual-wavelength absorption detection may be considered to fall within the field of optical detection; however, the methods and apparatus discussed herein may also include absorption detection in the ultraviolet and infrared region as well as the visible region of the spectrum. Dual-wavelength absorption detection is based upon the Lambert-Beer law which states that the amount of light absorbed by a given substance in solution (Absorbance) is proportional to the intensity of incident light and to the concentration of the absorbing species. This is expressed mathematically as:

$$A = abc = \log I_0/I = \log 1/T \quad (1)$$

where:
A = absorbance,
a = molar absorptivity in liters per mole-centimeter,
b = light path length in centimeters,
c = concentration of substance in moles per liter, It may also be expressed as a log ratio between a non-absorbing species and an absorbing species where:

$I_0$ = intensity of radiation detected with a nonabsorbing sample placed along a light path of length "b" at a certain wavelength, I = intensity of radiation detected with an absorbing sample having a concentration "c" placed along the light path of length "b" at the same wavelength, and $T = I/I_0$ = transmittance.

The Lambert-Beer law requires the use of a single beam, single-wavelength detector to provide a measurement of "absorbance" for the absorbing species when a nonabsorbing species is used to establish the reference level of illumination. One widely used variation from the Lambert-Beer law may be used in analytical chemistry to provide an approximate indication of the absorbance of a species at a specific wavelength without using a second nonabsorbing species to establish the reference level of illumination. The resulting measurement may not be an exact measurement of absorbance as defined by formula (1) because this variation does not rigorously follow the Lambert-Beer Law; the measurement using this variation is referred to in analytical chemistry as an "absorption" measurement. This widely used variation is called single beam, dual-wavelength, absorption detection. In this variation, a single sample or species is irradiated with a beam having at least two different wavelengths, a measuring wavelength and a reference wavelength, preferably the source supplies the wavelengths to have equal intensity. The measuring wavelength is selected in the region of the spectrum where the species to be monitored absorbs, whereas the reference wavelength is selected where the species has little or no absorbance. The measuring wavelength would be approximately equivalent to the "I" of formula (1), the reference wavelength would be approximately equivalent to "$I_0$" of the formula, and the log of the ratio $I_0/I$ is in units of "absorption". Preferably, the two wavelengths would be selected to be near each other in the spectrum.

In some dual-wavelength absorption measurements, the reference wavelength may have some absorbance in the species but to a lesser extent than the measuring wavelength. In this case, the absorption measurement would reflect the log ratio of the difference in the absorption of optical energy by the species at both wavelengths. Thus, with a known chemistry, the detected "absorption" value of the species, i.e., the value or amplitude of the output signal using a particular detector, would be a known amount. If there is a deviation from this known absorption value, then the chemistry of the species would have changed.

The single beam, dual-wavelength, absorption detector is widely used for performing chemical analysis involving the sampling of a consecutive flow of materials passing through the detector. FIG. 1 depicts the output of such a detector over time. Absorption peaks 1 through 8 represent the absorption values of various species which are separated in the continuous-flow sample stream by a volume of carrier solvent. A carrier solvent does not exhibit any absorbance at either the measuring or reference wavelength. This type of detector has a single flow cell (also referred to herein as a sample cell) where the sample in the flow stream is subjected to radiation at both wavelengths. An apparent advantage in using this type of detector is that factors which affect the intensity of one wavelength, other than absorption of optical energy by the sample, would similarly affect the other wavelength. However, in spite of this advantage, typical single beam, dual-wavelength configurations for absorption detection in a continuous-flow sampling system may have inherent limitations which affect its ability to detect absorption efficiently and accurately. Some of these limitations may be found in the typical continuous flow cell, the source of optical energy and the requirement that electrical components and flow components of the absorption detector be placed in close proximity to each other.

Prior art FIGS. 2A and 2B illustrate simplified arrangements used in typical single-beam, dual-wavelength absorption detector for irradiating a sample material (species) in a continuous-flow detector-cell and for detecting the illumination which has been subjected to the sample material. The term "detector-cell" is used herein to avoid confusion with another term "detector".

The term "detector-cell" in this specification includes the sample cell and the components associated with it, e.g., a means for source radiation to enter the cell to irradiate the sample, a means for illumination that was subjected to the sample material to exit the sample cell for detection, and a means for the sample material (species) to enter the sample cell; whereas, the term "detector" includes the detector-cell and any other components, including electronics, necessary to produce a signal which is representative of the absorption of the sampled material.

FIG. 2A is a simplified representation of a detector-cell having a continuous-flow sample cell $10a$ located between a source of optical energy 12 and a photodetector (photodiode or phototransducer) 14. In this arrangement, optical energy is transmitted inline with the sample flow. The length of the optical energy path within the sample cell determines the sensitivity of this absorption detector. The longer the optical path is within the sample cell, the greater the detector's sensitivity to differences in the absorption of optical energy between the measuring wavelength and the reference wavelength.

In FIG. 2A, sample cell $10a$ is shown in a vertical-longitudinal cross-section. This particular sample cell $10a$ is known as a "Z" flow-through channel structure. Other channel geometries are possible, for example, FIG. 2B illustrates in vertical-longitudinal cross-section another widely used flow-through sample cell $10b$ which has a "U" structure. The directions of flow in sample cells $10a$ and $10b$ are indicated by the arrows. The optical energy enters the sample cell in each of the FIGs. at window 16 and exits by window 18.

These flow cells ($10a$ and $10b$), shown in FIGS. 2A and 2B, are commonly used, but in order for optical radiation to be transmitted inline with the flow path of the sample material, the sample has to follow a tortuous path of flow into and out of the sample cell. One frequent problem with detectors having these types of sample cells is that they are subject to bubble noise. Often the species may have entrained gas bubbles or air bubbles. Bubble noise is caused by the bubbles becoming trapped within the sample cell due to the tortuous path of the sample through the flow cell. The natural buoyancy of the bubble in the fluid may cause it to contact and to adhere to a wall of the flow cell. When the pumping system does not provide enough flow to overcome the adherence and the friction between the bubble and the wall, it may be difficult to dislodge the bubble from the flow cell. The pumping system then causes the bubble to pulsate between pumping cycles, thus causing pulsations in the illumination intensity at photodetector 14.

One solution to the bubble problem is to use another arrangement for the sample cell as shown in FIG. 2C. This sample cell $10c$ is a straight flow-through cell aligned vertically such that the optical energy is transmitted across the cell, i.e., transverse to the flow. However, in order to maximize sensitivity, the cell is broadened to increase the optical path length. By increasing the optical path length, the volume of the cell is increased. This increases the dead zone of the sample cell. A larger dead zone requires that the individual samples have larger volumes for adequate separation from other samples and to prevent the sample from mixing in the sample cell. This results in reducing the total number of samples that may be done in a given time period and also results in broader absorption peaks, as depicted in absorption peak 1 of FIG. 1, because the sample remains in the sample cell longer.

If the optical path length is decreased to reduce the volume of the cell, the sensitivity of the detector is reduced. For example, assuming everything else remains the same, if the optical path length is halved, then the amount of absorption of optical energy is substantially reduced in both wavelengths, thereby reducing the ratio between the reference and measuring wavelength. Consequently, the output signal (absorption measurement) may be reduced by as much as a half. This is illustrated on FIG. 1, where in this case, the amplitude of the output signal would be represented on a recorder as peak 3, instead of peak 4. Sensitivity is particularly important when a heavily diluted sample is used which does not readily absorb at the measuring wavelength. For example, peaks 6, 7, and 8 on FIG. 1 represent a dual-wavelength sample measurement which has relatively low absorption measurement. If the optical path length were to now be decreased by one half, the peaks may be indistinguishable from noise if the sample line was subject to bubble noise or other forms of noise present in a plant environment.

There are other limitations with the arrangements shown in FIG. 2A, 2B and 2C. Because the light source 12 and photodetector 14 are on opposite sides of the flow cell 10, these arrangements may not effectively utilize the light (radiation) produced by the source, i.e., they do not exhibit high coupling efficiency for collecting light. Light upon entry into the flow cell through window 16 will fan-out (diffuse). Diffusion of light may result from numerous causes. Primarily, in this case, it results from the source producing a beam of light having rays which originate from a plurality of point sources. And, all of these point sources are not aligned so that when the rays of each point source enter the inlet window (window 16), the rays are not exactly aligned with the length of the flow cell and the outlet window 18. Additionally, other forms of diffusion also occur; these forms include: (1) refraction of light as it crosses material boundaries, (2) scattering of light due to particles along the path length and (3) the tendency of light to spread out normal to its path of movement (Beam spreading).

If the flow cell is narrow, as shown in FIGS. 2A and 2B, some light, due to the fan-out (diffusion), may be absorbed in the walls or blocked by the walls of the flow cell. If the flow cell is wide, as shown in FIG. 2C, only a limited portion of the light upon entry into the inlet window 16 will be directed at window 18. If large amounts of optical energy are lost within the flow cell, then the detector will have a reduced ability to detect weak, e.g., strongly absorbed, illumination at the detector. The weakest signal that can be detected by the detector is limited by the "dark" current (noise) produced by the photodetector. As the illumination becomes weaker, the signal to noise ratio is reduced until a point is reached where it is not possible to distinguish between the signal produced by the weak illumination and the noise.

The signal to noise ratio between the detected illumination and the dark current may be increased by increasing the magnitude of the optical energy entering the sample cell. Increasing irradiating illumination increases the maximum repeatable ratio of reference illumination to measuring illumination that is detectable above the noise. However, increasing the amount of light transmitted into the flow cell could also result in increasing the temperature of the sample. Sample heating could cause chemical reactions or bubbles to come out of solution resulting in the sample no longer being representative of the material sampled.

The windows 16, 18 of FIGS. 2A, 2B, and 2C are also sources of inherent design limitations. They may be an integral part of the flow cell or they may be removable. In any case, they become dirty or scarred from the sample material. This reduces the performance of the absorption detector. The flow cell or the separately attached windows must be cleaned or replaced. Whether the windows are an integral part of the flow cell or separately attached, the windows are difficult to inspect, clean or replace in typical detector-cell arrangements.

Safety concerns related to electrical components of the detector-cell and ageing of the optical energy source also affect the utility of this type of detector. The cost to install this absorbance detection system could be expensive due to the expenditures necessary to meet fire and building codes. These safety codes are necessary because: (1) the sample cell may contain hazardous and/or explosive materials when sampling, and/or (2) the detector's electrical circuitry, which powers the optical energy source and the photodetector, could ignite hazardous or explosive vapors in the local area or vapors from the sample cell. When the arrangements shown in FIGS. 2A, 2B and 2C are used for in-plant monitoring, the radiation source, the photodetector and the detector-cell are housed in separate compartments with the compartments being located adjacently to, and inline with, each other so that optical energy may be transmitted between the compartments. The need to locate these components near each other and within the line of sight of each other, yet separate them to meet safety codes, substantially reduces the options available in locating an absorption detector within a processing environment.

In addition, many dual-wavelength absorption detectors use an optical energy source which has a wide frequency band. Special optical components such as optical filters and beam splitters are necessary to separate the reference and sampling wavelengths to determine the absorption thereby increasing the cost of the instrument. Also, as the wide band frequency source ages, the relative power levels of the frequencies within its spectrum change. This is called frequency spectrum shift and results over time in reducing the validity of dual-wavelength absorption measurements.

A simple, compact, robust and inexpensive dual-wavelength absorption detector is needed which features a configuration that (1) reduces bubble noise, (2) compensates for and utilizes the diffusion of source illumination, (3) allows easy access to the windows for inspection or replacement, (4) increases the sensitivity of the detector without increasing the dead zone of the sample cell and (5) provides for greater selectivity in locating absorption detector components to meet safety codes.

SUMMARY OF THE INVENTION

An object of this invention is to provide a dual-wavelength absorption detector which has been adapted to reduce bubble noise and compensate for and utilize the diffusion of source illumination in the detection of absorption for sample material flowing through a continuous-flow sample cell.

Another object of the invention is to provide a continuous-flow detector-cell having easy access for inspection and/or replacement of a sample cell.

A further object of the invention is to provide a detector-cell which increases the sensitivity of the detector without increasing the dead zone of the sample cell.

An additional object of the invention is to provide for greater selectivity in the locating of a dual-wavelength absorption detector by enabling the detector-cell to be separated from the electrical components of the detector.

Another object is to provide a method to detect absorption using sequential dual-wavelength illumination of a continuous-flow sample which (1) reduces bubble noise, (2) compensates for and utilizes the diffusion of the dual-wavelength illumination and (3) increases the sensitivity of the absorption measurement without increasing the dead zone of a sample cell.

In accordance with the objects of this invention, there is presented a dual-wavelength absorption detector which uses a multi-branched optical guide to connect an electronics section with a detector-cell. The invention is adapted such that the detector-cell uses only a single connection location with the optical guide. The single connection location has two functions: (1) it acts as a location to provide optical energy to irradiate sample material within the detector-cell, and (2) its acts as a location to collect illumination which has been subjected to the sample material. By using the optical guide, it is possible to separate the detector-cell from the electrical components of the detector for greater selectivity in locating components which make up the dual-wavelength absorption detector to meet safety codes.

In preferred embodiments, a trifurcated optical guide is used. Each branch has a plurality of fibers (strands) which are combined at one end of the guide into a single bundle of fibers to provide a common end. In one embodiment, fiber ends of the fibers in the common end may be arranged in a random order. In another embodiment, the fiber ends for each branch may be grouped together such that one group of fibers is placed at the center of the common end with the remaining groups of fiber ends forming concentric rings around the center group. In still another embodiment the fiber ends of the branch fibers may be equally distributed across the common end. At the other end of the optical guide, the three branches are separated with the fibers of each branch being terminated at separate locations within the electronics section. Two of the branches are each located adjacently to a light emitting diode (LED).

When pulsed, one LED produces light having a sampling wavelength and the other LED produces light having a reference wavelength. The remaining branch of the optical guide is terminated adjacently to a photodetector.

The common end is connected to the detector-cell such that its fiber ends are located at a fixed location which is adjacent to an approximately vertically aligned continuous-flow sample cell. In one preferred embodiment, the sample cell has two flat parallel sides with the flat sides being approximately transverse to the fiber ends. A concave mirror is located on the opposite side of the sample cell from the optical guide connection.

The electronics section has logic drivers which pulse the LEDs sequentially to emit light. These pulses of light are guided through the LED's respective branch of the optical guide to the common end. There, the pulses diffuse across the sample cell, where some of the pulses' light is reflected back across the sample cell by the concave mirror. Within the sample cell, optical energy from the pulses having the sampling wavelength are absorbed by the sampling material to a greater extent than optical energy having the reference wavelength. The concave mirror concentrates the reflected pulses by reflecting the illumination toward the fixed location where it is to be collected by the common end; thus, the mirror enables the detector to more efficiently utilize optical energy which has diffused across the sample cell. Also, the concave mirror at least doubles the optical path length of the optical energy, thereby increasing the sensitivity of the flow cell without increasing the dead zone of the sample cell. Additionally, the concave mirror in conjunction with the common end enables the detector-cell to utilize a single location adjacent the sample cell to irradiate the sample and to collect illumination which has been subjected to the sample.

Reflected light striking the photodetector branch ends are collected and guided to the photodetector where the detector sequentially produces a signal for each wavelength. The signal is proportional to the intensity of the illumination striking the photodetector fiber ends. The signal is then sent to a sample and hold circuit which is associated with the particular LED that was pulsed on to produce the signal. Then, the signal for the other wavelength is obtained in another sample and hold circuit. The signals are then compared in a log ratio amplifier which provides an output proportional to the absorption of the sample material.

In preferred embodiments, the reflection characteristics of the mirror are selected in consideration of the location of the fiber ends (the fixed location), the mirror's location, and the refraction of light along the optical paths between the fiber ends and the mirror. In a highly preferred embodiment, the concave mirror is a spherical mirror with the fixed location for the fiber ends being at the center of curvature of the mirror (the focal point) for the spherical mirror.

Other embodiments are also possible, for example, additional branches could be added to the optical guide, each additional branch being associated with an additional LED having a different wavelength from the other LEDs, and the electronics section could be arranged to provided absorption measurements for a plurality of different dual-wavelength combinations.

These and other objects and advantages of the present invention will no doubt become apparent to those of skill in the art after having read the following detailed description of the preferred embodiments which are contained herein and illustrated by various figures.

The invention encompasses the heretofore described preferred embodiments as well as the embodiments as are described hereinafter and as will be apparent to those of skill in the art.

DESCRIPTION OF EMBODIMENTS

Figure 3:
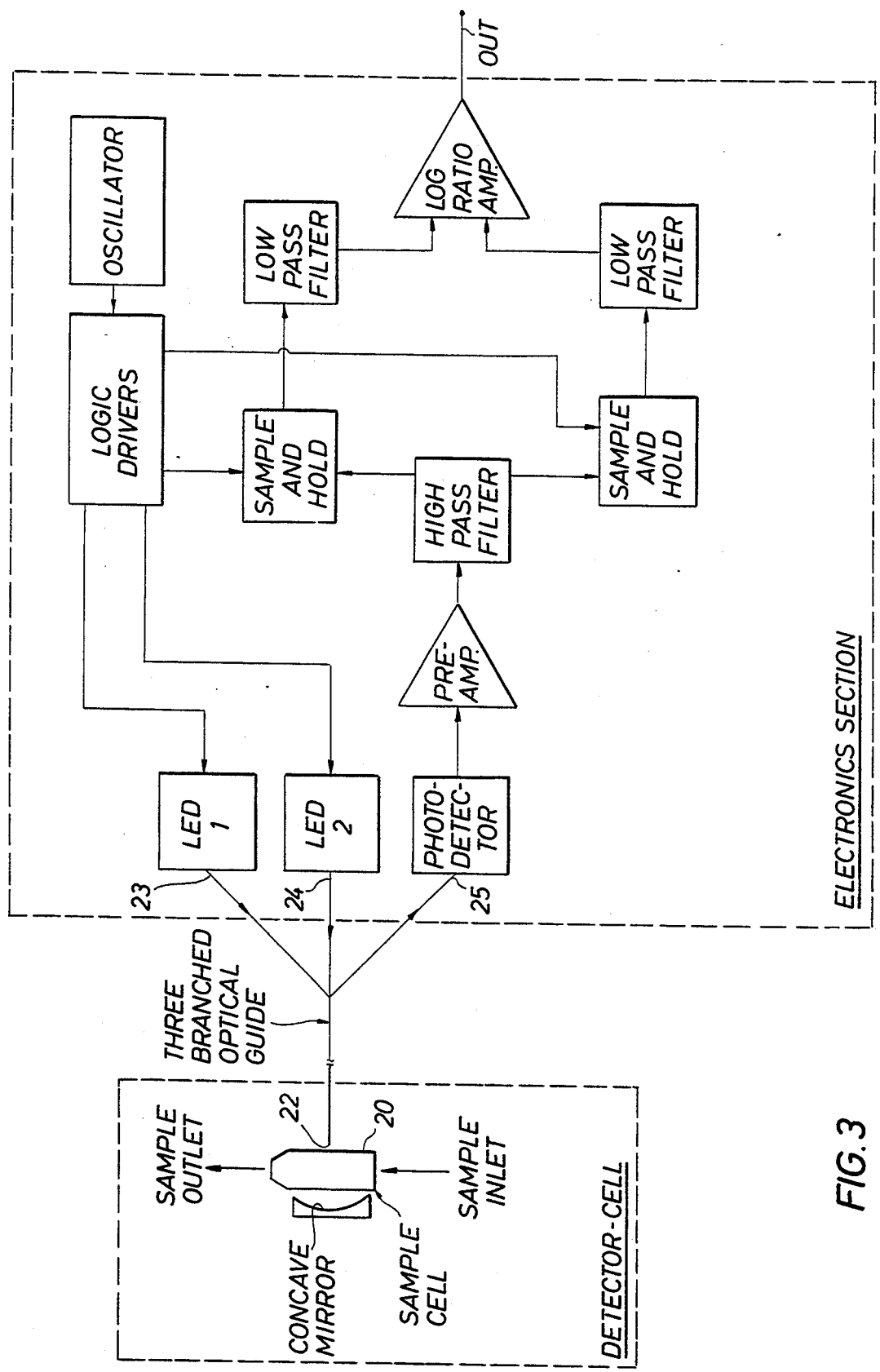
FIG. 3 is a simplified illustration showing the optical and electrical arrangement of one embodiment of the invention, the optical arrangement being shown in a simplified side view and the electrical arrangement being shown in block diagram.

One embodiment of a dual-wavelength absorption detector adapted for continuous flow detection and having a single point connection within the detector-cell for the transmission and collection of optical energy is shown in FIG. 3.

FIG. 3 shows this embodiment to include a detector-cell (shown in simplified vertical cross section), an electronics section (shown in block diagram) and a three (3) branched (trifurcated) optical guide connecting the detector-cell with the electronics section.

The detector-cell includes an approximately longitudinal, vertically aligned sample cell 20 having a bottom inlet and a top outlet. The openings enable the sampling system to supply a continuous-flow of sample material into the detector-cell. This approximately vertical alignment of the sample cell 20 prevents bubbles from remaining within it. A concave mirror is located on the opposite side of the flow cell from the optical guide connection.

In the embodiment of FIG. 3, the three branched optical guide has a plurality of fibers (strands) which are divided into three branches. Preferably, each branch also has a plurality of fibers, although it is possible for some embodiments of this invention to contain a single optical fiber in each branch. The fibers of the three branches are combined at one end of the optical guide into a single bundle of fibers having a common end 22.

The common end is connected to the detector-cell such that its fiber ends 22 are held at a fixed location adjacent to the sample cell 20. At the opposite end of the optical guide, the three branches are separated to form three distal ends 23, 24, and 25 for connection to the electronics section. Two of the three distal ends 23, 24 are connected to the electronics section adjacent to light emitting diodes (LEDs). The fibers in these branches will be referred to as LED fibers. These two branches guide light within their fibers from the LEDs to the detector-cell. The remaining distal end 25 is connected to the electronics section adjacent to a photodiode (photodetector or phototransducer). Fibers within this branch will be referred to herein as photocell fibers or photodetector fibers. This branch guides light which strikes the fiber ends of the photodiode fibers from the detector-cell to the photodiode within the electronics section.

The electronics section has logic drivers which pulse the light emitting diodes (LED 1 and LED 2) at selected sampling rates to cause them to transmit alternating pulses of light (alternating beams) into their separate branches of the three branched optical guide. Light emitting diodes have been shown to have a limited bandwidth with fairly stable frequency characteristics over time; thus, by selecting LED's having the desired measuring and reference wavelengths, it is possible to provide the two wavelengths necessary to obtain absorption measurements without having to use optical components to separate measuring and reference wavelengths from a wide frequency spectrum. In other embodiments, laser diodes may also be used.

As the pulsed wavelengths of light (pulses) leave their respective LED fibers to pass into the sample cell 20, the pulses diffuse. Some pulsed light, after traveling across the sample cell 20, is reflected back across by a concave mirror such that this reflected light strikes the fiber ends 22 at the fixed location.

Reflected light pulses striking the photocell fiber ends are guided to the photodetector where they are converted into an electrical signal (voltage or current) that is proportional to the intensity of reflected light striking the photodetector (photocell) fiber ends. The signal is then amplified and passed through a high pass filter where frequencies less than the frequency of the pulsing rate are attenuated. From the high pass filter, the signal goes to a sample and hold circuit. Each sample and hold circuit is associated with a particular LED and is turned on to receive the signal resulting from the pulsing of its respective LED. The signals are then passed through a low pass filter to remove any frequencies above the sampling modulation frequency and compared in a log ratio amplifier which provides an output signal which is proportional to the absorption measurement.

When operating at a 100 per cent or even a 50 per cent duty cycle, an LED may not produce enough light to effectively determine absorption over a wide range of values because drive currents must be maintained below certain values to insure that the diodes do not overheat and fail. However, in some preferred embodiments, the LED's are pulsed at a low duty cycle, e.g., a duty cycle of less than ten percent, and at pulsing rates of between 500 and 2000 Hertz. The preferred pulsing rates enable the output signal from the electronics section when displayed on a recorder to appear to be continuous. The low duty cycle enables operation of the LEDs, in these embodiments, at higher drive currents than permitted when the LEDs are operated at a 100 or 50 percent duty cycle. The higher drive currents increase the amount of light emitted while the low duty cycle allows each LED to cool between light emissions; thus, the higher drive currents do not result in premature failure of the LEDs. In addition, the low duty cycle also enables the sample to cool between light emissions; thus, even though irradiation of the sample is significantly increased for short periods of time, the sample is not subjected to heating which could alter the properties of the sample material. The minimum duty cycle is determined by several factors, among them are the turn-on and turn-off times of the LEDs or other electronic components and the ability of the photodetector to respond to the shorter time spans. There is an upper limit on the amount of drive current which may be obtained by reducing the duty cycle to reduce heating; however, in some highly preferred embodiments duty cycles of between 0.1 and 4% have been obtained with substantial increases in the drive current without reducing the life of the LED.

The use of the optical guide (fiber optic cable) enables the electrical components to be separated from the detector-cell; thus the components no longer have to be near each other or within line of sight of each other and this also allows all of the electrical components to be placed in the same housing. In addition, sampling material which might present a substantial explosive hazard in the presence of electrical sparks could be separated completely from the electrical portions of the detector using widely separated cabinets. Consequently, there is greater flexibility in meeting safety codes.

Figure 4:
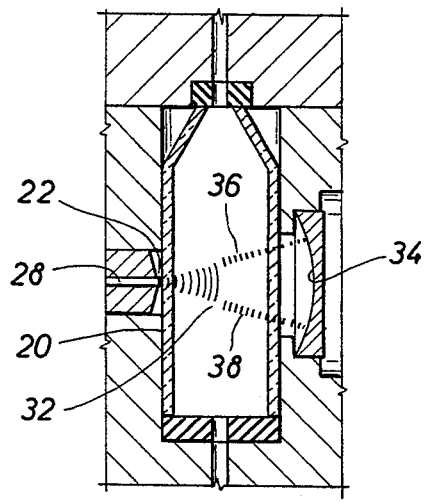
FIG. 4 is a cross sectional illustration showing diffusion of optical energy across a sample cell.

FIG. 4 is a cross-sectional illustration to show the diffusion of optical energy across sample cell 20 and how the single connection within the detector-cell for both light transmission and light collection enhances the utilization of optical energy in this invention. As mentioned previously, the fibers for each branch are combined to form a single bundle of optical fibers 28 having a common end 22. The common end is terminated within the detector-cell. The common end's fiber ends 22 are fixed in place next to the flow cell (sample cell) 20.

As optical energy of either wavelength (represented by 32 in FIG. 4) leave the LED branch fibers (the illumination source location), it diffuses as it crosses the sample cell 20. Much of the diffusion is dependent upon the characteristics of the optical fibers used. In typical fiber optic cable, depending upon the numerical aperture rating of the fiber, the angle of fan-out of the pulsed light as it leaves each fiber could range between 12 and 62 degrees. The numerical aperture rating also specifies the angles by which the fiber collects light. Additional diffusion occurs as the light crosses the cell. This additional diffusion results from refraction at each different material boundary, e.g., the walls of the sample cell and the sample material, beam spreading and scattering.

In typical operations, optical energy having the measuring wavelength will be absorbed by the sample to a much greater extent than optical energy having the reference wavelength as it moves through the sample. When the light reaches the opposite side of the cell, this fanned-out (diffused) pulse of optical energy will encounter the concave mirror 34. The concave mirror will reflect much of the optical energy (represented by 36 and 38 in FIG. 4) from a plurality of reflection points back into and across the sample cell such that the reflected optical energy is concentrated (or focused) in proximity to the fixed location (the common end 22).

Each reflection point on the mirror, will return reflected light approximately along the same path the light followed to strike the mirror. Upon reencountering the material boundaries, the reflected light will again be refracted such that the angle of this refraction will be approximately the reverse of the initial angle of refraction when the light first encountered this boundary. Since the light is not, in all cases, reflected exactly back along the path it took to arrived at the mirror or refracted during the recrossing at exactly the reverse of the initial refraction angles, all of the light does not return exactly to the same point it left the common end. However, because the light from each reflection point is also subject to beam spreading and beam scattering, a substantial amount of reflected light will be concentrated (focused) near the fixed location where some of this reflected light will strike the photocell fiber ends.

Figure 1:
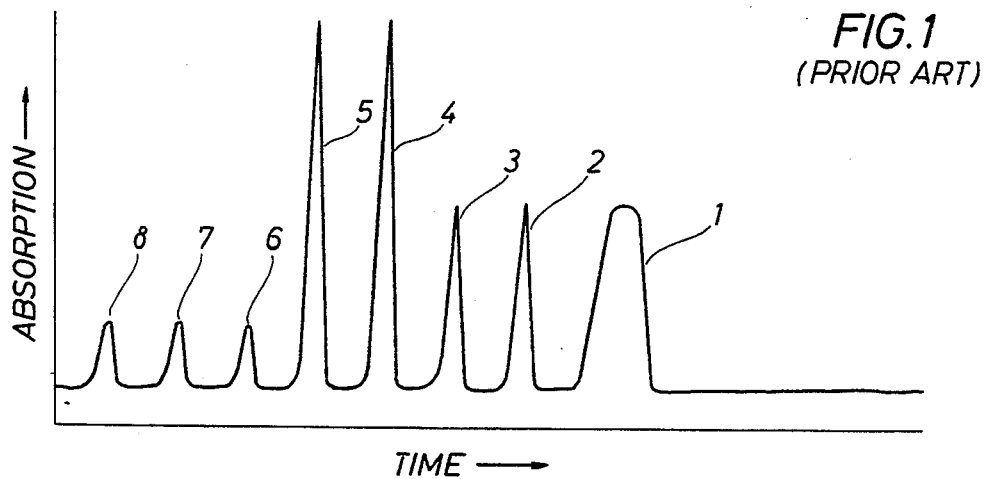
FIG. 1 is a prior art illustration depicting absorption vs. time of sampled material separated by carrier solvent.
Figure 2A:
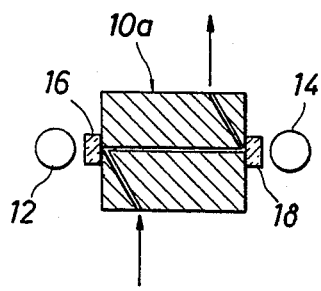
FIG. 2a is a simplified prior art illustration of an absorption detection arrangement having a "Z" flow cell for a sample cell used in a continuous flow sampling system.
Figure 2B:
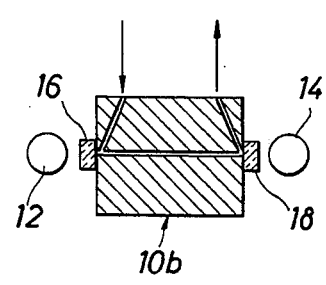
FIG. 2b is a simplified prior art illustration of an absorption detection arrangement having a "U" flow cell for the sample cell used in a continuous flow sampling system.
Figure 2C:
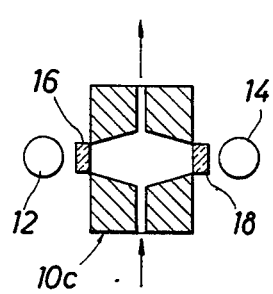
FIG. 2c is a simplified prior art illustration of an absorption detection arrangement having a "vertical" flow cell for the sample cell used in a continuous flow sampling system.

This single point connection arrangement with the concave mirror enhances light (optical energy) utilization in two ways. In one, it at least doubles the sensitivity of the detector without increasing the dead zone of the sample cell as compared to the typical detector-cell arrangements shown in FIGS. 2A, 2B and 2C. In the other, the design reduces light losses by using the concave mirror to intercept, reflect and concentrate (focus) the light such that substantially less light is lost from diffusion than in the previously mentioned prior art; there, much of the illumination which was not directly on the axis between the sample cell's windows was lost. Consequently, it was not collectable.

The total intensity of the light carried by each branch is based, in part, and assuming all else remains constant, upon the total number of fibers in each branch; thus, for example, if the amount of light collected by and guided within the photocell branch is insufficient, the number of fibers in that branch may be increased. In embodiments where glass fibers cause substantial attenuation at either of the dual-wavelengths, the fibers may be selected from materials such as silica, sapphire, fluoride or some other material, depending upon cost factors and the wavelengths used, to reduce attenuation.

Figure 4A:
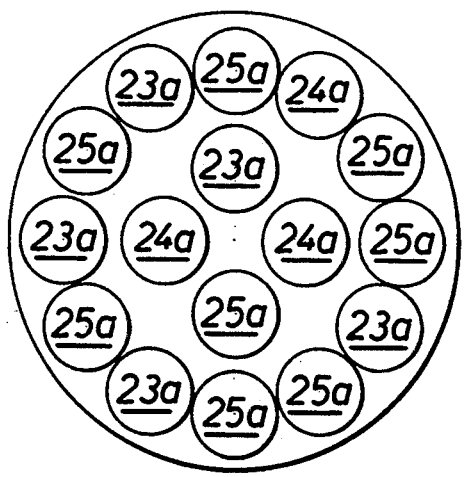
FIG. 4A is a cross sectional illustration of fiber ends having a random distribution of the fiber ends across the cross section.
Figure 4B:
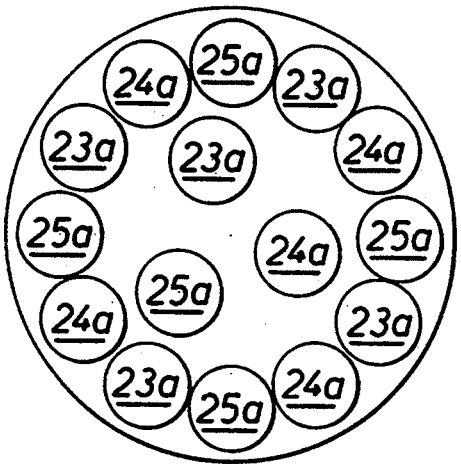
FIG. 4B is a cross sectional illustration of fiber ends having an evenly distributed order of fiber ends across the cross section.

In one embodiment, the strands of optical fiber in each of the three branches are randomized when combined to form the single bundle of fibers; thus, at the fixed location, the fiber ends are arranged in random order across the common end. This is illustrated in FIG. 4A. There, a cross section of the common end 22 shows LED 1's fiber ends 23a, LED 2's fiber ends 24a, and the photodetector's fiber ends 25a arranged in random order across the cross section. In another embodiment, the fiber ends are arranged such that all of the fibers ends are approximately equally distributed across the common end. This is illustrated in FIG. 4B. There, a cross section of the common end 22 shows LED 1's fiber ends 23a, LED 2's fiber ends 24a, and the photodetector's fiber ends 25a arranged in an evenly distributed order across the cross section. In still another embodiment, each branch's fiber ends could be grouped such that one branch has its fibers grouped at a center of the common end while the remaining fibers are grouped to form concentric rings about the center group. In other embodiments, the LED's fibers could have a numerical aperture rating which reduces the fan-out of light and the photodetector fiber could have a numerical rating which allows each fiber end to collect light from greater angles than the LED fiber ends.

Figure 3A:
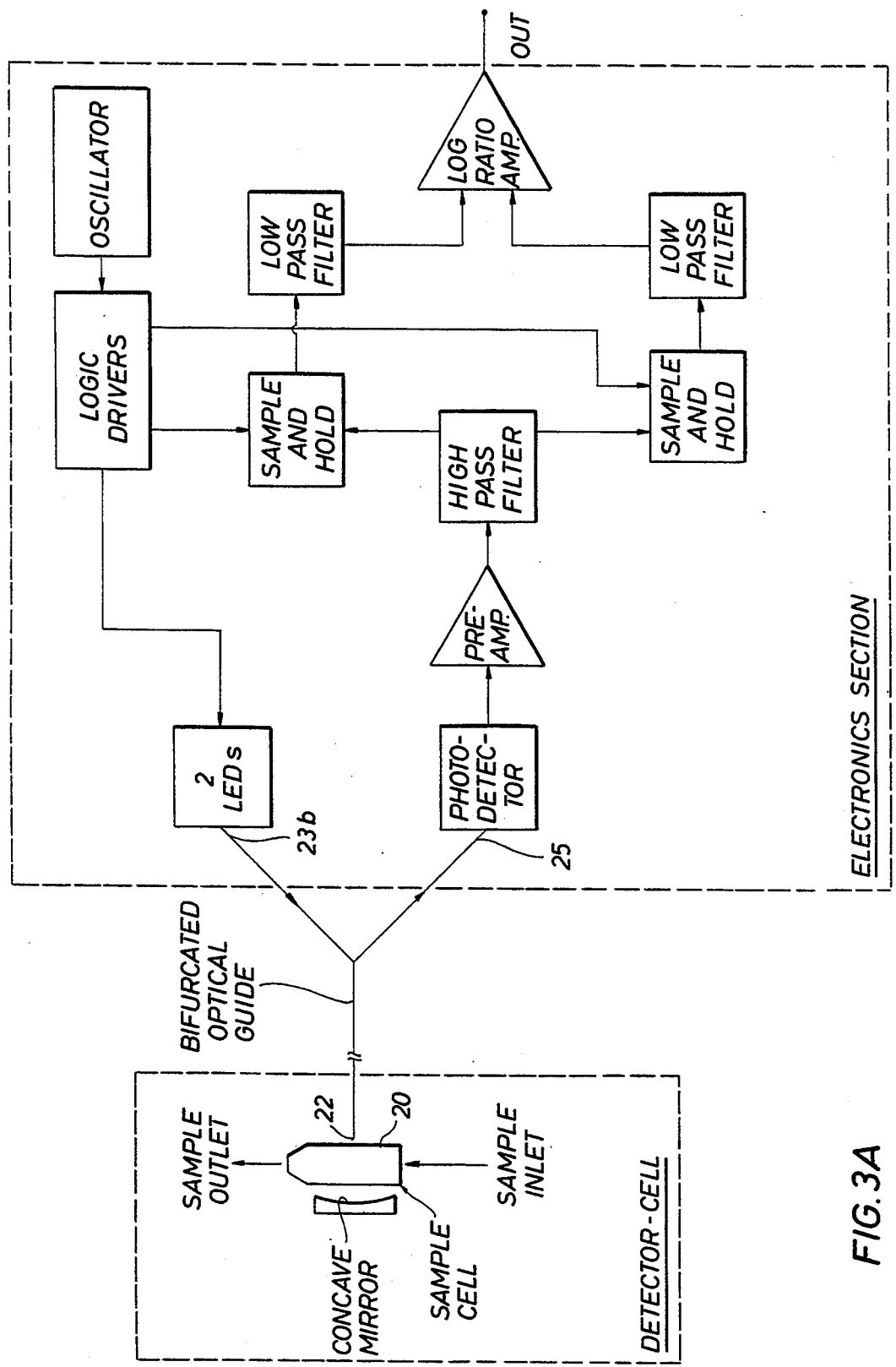
FIG. 3A is a simplified illustration similar to FIG. 3 showing a bifurcated optical guide and an electronics section block diagram for an embodiment which uses two LEDs mounted together.

Other embodiments are possible for the optical guide. As one example, which is illustrated by block 23b in the electronics section of FIG. 3A, two LEDs may be mounted together and pulsed sequentially (alternately). Or, instead of using the two LEDs mounted together in block 23b a single two-color LED could be used for block 23b with the colors being pulsed sequentially. In these cases, only a two branched (bifurcated) optical guide is needed for the detector because only one branch is necessary to guide the sequential pulsed light to the detector-cell. Additionally, more LEDs may be added to the absorption detector along with corresponding optical guide branches to guide the additional wavelengths to the detector-cell. The electronics could then be arranged to determine a plurality of absorption values from a plurality of dual-wavelength combinations.

In selecting the concave mirror of some embodiments, the concave mirror's reflection characteristics are selected with respect to the refraction characteristics of the material boundaries between the fiber ends and the mirror's location, e.g., the sample cell and the sampling material boundaries, the mirror's location, and the location and numerical aperture of the fiber ends. In one highly preferred embodiment, the concave mirror is a spherical mirror with the fixed location (the location of the common end) being at the center of curvature of the mirror (the focal point) of the spherical mirror. Other embodiments are also possible, for example, in one embodiment, methods may be used to vary the fixed location of the common end in increments during calibration to identify the fixed location at which illumination on the photodetector fiber ends for a particular mirror and/or sample material is maximized. In another, a lens may be used in conjunction with the sample cell to focus illumination to and from the fiber ends.

Figure 5:
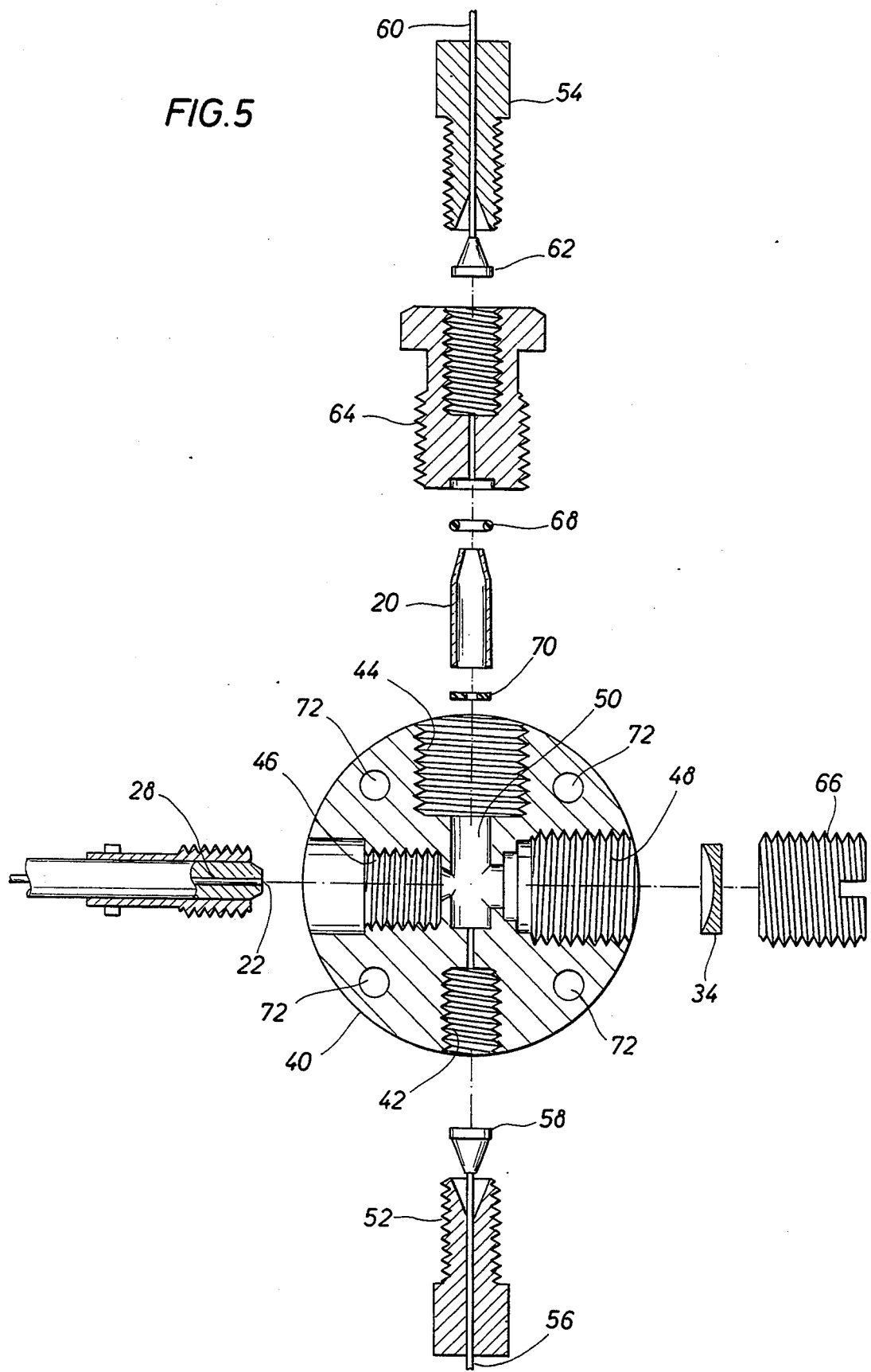
FIG. 5 is an exploded view showing a vertical cross section of one embodiment of the detector-cell assembly.
Figure 6:
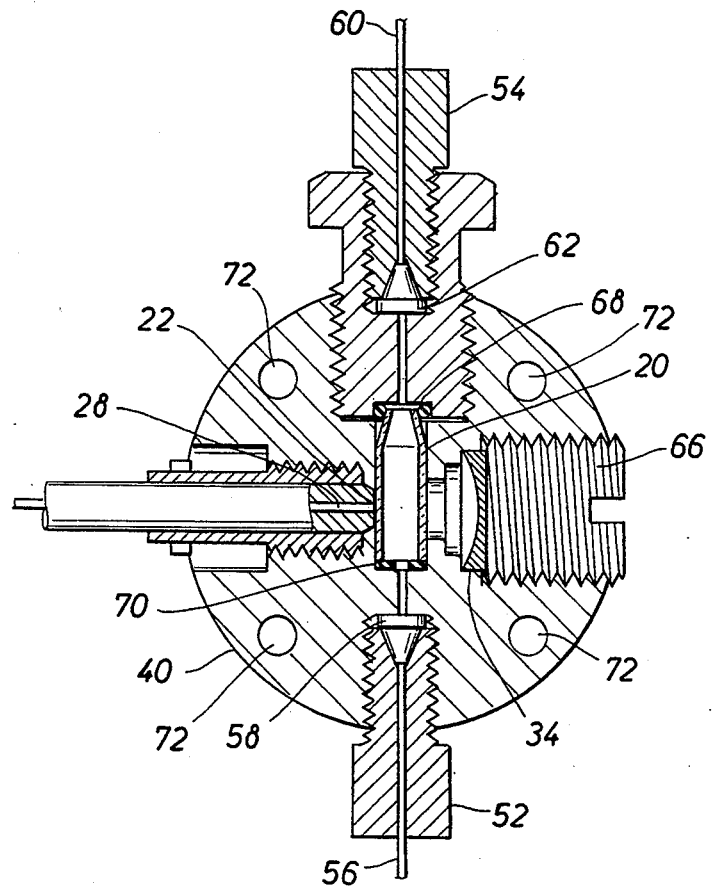
FIG. 6 is an assembled view of the exploded view of FIG. 5.

Referring now to FIGS. 5 and 6, FIG. 5 is an exploded vertical-horizontal cross sectional view of one embodiment of the detector-cell shown in simplified form in FIG. 3. And, FIG. 6 is an assembled cross sectional view of the detector-cell shown in FIG. 5. In some embodiments, the body 40 of the detector-cell may be machined from a single block of material. In one highly preferred embodiment, the body as well as most of the associated fittings are made from PEEK (polyetheretherketone). In other embodiments, it may be necessary to use other materials in order to meet the building code requirements due to particular explosive and fire hazards inherent in the substance being sampled with respect to the area where sampling is conducted.

Returning to FIGS. 5 and 6, the body 40 of the detector-cell contains four openings 42, 44, 46, and 48. All openings open into a central cavity 50 within the body which holds the sample cell 20. Openings 42 and 44 are used to connect the body to screw fittings 52, 54 which tie the detector-cell to a sample line. Sample line input fitting 52 includes a line 56 from the sample system running through the fitting and connecting to a ferrule 58. Output line fitting 54 has a similar arrangement with the output sample line 60 running through the fitting 54 and connecting to ferrule 62. However, fitting 54 does not connect directly to the body 40, but connects to a sample cell inspection titling 64. This fitting 64 is used to provide access to sample cell 20 so that it may be easily inspected or replaced.

Opening 46 provides for the connection of the bundle of fibers 28 to the body 40 such that the common end's fiber ends 22 are held at the fixed location adjacent to the sample cell 20. In one preferred embodiment, opening 46 is machined to be compatible with a standard optical ST-type connector. The bundle of fibers 28 is then fitted with a standard optical ST-type connector to provide quick and repeatable re-connections of the optical guide to the detector-cell such that the fiber ends 22 are fixed with respect to the concave mirror 34 mounted within opening 48. Screw 66 aligns and holds mirror 34 in place and allows removal of the mirror for inspection of the flow cell. The mirror may also be removed for change out of the mirror if different reflection characteristics are desired. For example, a change in the refraction index of the sampling materials may require a concave mirror with different reflection characteristic for reflecting and focusing the reflections. Additionally, the mirror may be removed for calibration checks. With the mirror removed, a determination of the light reflected from the sides of the flow cell may be possible so that adjustment (calibration) of the electronics section may be made for light which enters the photodiode fibers but has not been subjected to the sample material along the entire optical path length.

Figure 7:
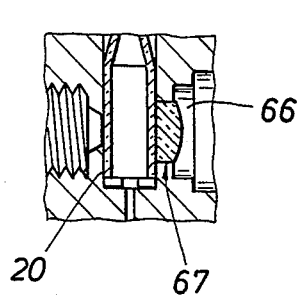
FIG. 7 is a partial side view of a detector-cell showing a different type of concave mirror than shown in FIG. 6.

FIG. 7 is a cross sectional partial view of the detector-cell showing another type of concave mirror 67 which may be used for reflecting light. In this embodiment, one side of the mirror rests against the sample cell 20 with a reflective surface being located on the far side of the mirror from the flow cell, i.e., a second side reflection coating mirror. Here, the sample cell aligns the mirror and screw 66 holds it in place.

Figure 8C:
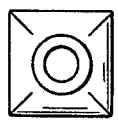
FIG. 8C is a top view of the flow cell embodiment of FIG. 8A.
Figure 8A:
FIG. 8A is a side view of one embodiment of a flow cell.
Figure 8A:
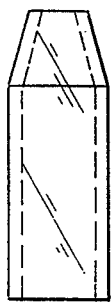
Figure 8B:
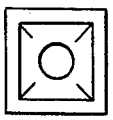
FIG. 8B is a bottom view Of the flow cell embodiment of FIG. 8A.

One preferred embodiment of sample cell 20 is depicted in FIGS. 8A, 8B and 8C. FIG. 8A is a side view showing the sample cell to have a tapered top. In one representative embodiment, the straight wall portion of the sample cell is approximately 8 mm (millimeters) with the length of the tapered walls being approximately 5 min. FIG. 8B is a bottom view of the embodiment of FIG. 8A. It shows this embodiment of the sample cell to have an approximately square bottom opening formed by the straight wall portions. In this particular embodiment, the exterior square cell walls are approximately 4.5 mm wide and the interior width of each cell wall is approximately 3.0 min. FIG. 8C is a top view of the embodiment of FIG. 8A. The tapered walls and corners of this embodiment are increasingly rounded so that the top opening in the sample cell is circular. In the representative embodiment having the dimensions stated, the volume of the flow cell is approximately 80 micro-liters.

Returning to FIGS. 5 and 6, and using a sample cell similar to the embodiment of FIG. 7A, the round exterior top surface of the sample cell 20, shown by example in FIG. 8C, is sized so that a standard commercial "o-ring" 68 may be used to provide a pressure seal at the top of the sample cell 20. This ensures that the top of the sample cell may be quickly and easily sealed. Between the sample cell 20 and the bottom of chamber 50, a gasket 70 is used to provide the pressure seal. In some preferred embodiments the gasket may be glued to the bottom of the sample cell 20 to enhance the pressure seal.

Figure 9:
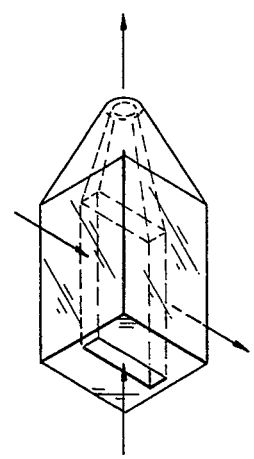
FIG. 9 is a perspective view of a sample cell having a narrow flow channel for sample material.

FIG. 9 shows in perspective another embodiment for a sample cell. One pair of arrows indicates the path of sample material though this flow cell from the bottom to the top. In this embodiment, the width of the sample cell's flow channel is narrowed to reduce the volume of the sample cell and decrease the dead zone. This is done by making the flow cell sides (walls) which do not face the mirror or the fiber ends thicker than the sides facing the common end. Another pair of arrows on FIG. 9 indicates a path for light to pass through the flow cell. In this embodiment, although the volume of the cell has been reduced, the sensitivity of the detector is not decreased since the length of the optical path length has not been shortened. Although the narrowing of the flow channel may reduce the amount of reflected light which may be detected, the use of flow cells having a standard exterior size and shape but different dead zones will enable a single detector-cell to be adapted quickly to provide absorption measurements based upon the size of the sample volumes available and the strength of the illumination provided.

In other embodiments, instead of being square shaped, the sample cell may be rectangular or have two rounded sides. However, it is highly preferred that the sample cell have two parallel flat sides with the flat sides being approximately transverse to the light radiation emerging from the common end.

In some embodiments, the sample cell is made from annealed quartz. In other embodiments, other materials may be used which have the necessary transparency to allow enough light at the sampling and reference wavelengths to be transmitted and reflected across the sample cell. Additionally, anti-reflective coatings may be used to reduce the amount of reflection from sample cell walls into the common end.

Returning to FIG. 5, preferably, chamber 50 is milled such that the sample cell 20 is self aligning within the chamber. In one preferred detector-cell embodiment having a sample cell with two parallel flat sides, the chamber is milled to ensure the proper alignment of the sample cell with the fiber ends 22 so that the flat sides are approximately transverse to the optical energy exiting the LED fiber ends. When the chamber is milled for self alignment, it is a simple matter to unscrew the fitting 64, to inspect or replace the sample cell and to have assurance that the cell is properly aligned with the end of bundle of fibers and the mirror. The implementation of the self aligning embodiment described in FIGS. 5 and 6 would allow a person to inspect the sample cell without tools since these associated fittings on the illustrated detector-cell may be removed by hand.

Additionally, since the electronics section may be separated from the detector-cell, in certain applications, e.g., FIA (flow injection analysis), the detector-cell may be made portable so that it may be moved from one location to another for convenience in a laboratory or for sampling at various processing locations without having to move the accompanying electronic section. In one embodiment, instead of using mounting holes 72, a magnet is placed on the detector-cell so that it may conveniently be supported without the necessity of mounting it to a wall or work bench by screws or other mounting methods.

Although, the embodiments presented have been discussed with respect to liquid samples, the embodiments of this invention may also be used with, or adapted to work with, continuous-flow gas sampling system.

While several embodiments of the invention have been shown and described, it will be understood that the invention is not limited thereto since many modifications may be made and will become apparent to those of skill in the art.

What is claimed:

1. A method for determining absorption of a species using dual-wavelength, continuous-flow chemical analysis whereby the method reduces bubble induced noise and provides for utilizing optical energy diffusion to enhance the capability of the method to determine the absorption of the species, comprising the steps of:

(a) aligning a longitudinal sample cell having an opening at each end to an approximately vertical orientation such that there is one opening on the bottom and one opening on the top;

(b) attaching a sample line to the bottom opening of the a sample cell;

(c) directing the species to flow through the sample line into the sample cell as a continuous-flow having a direction of flow such that the species flows from the bottom to the top of the sample cell, said vertical orientation of the sample cell enabling air bubbles within the species to quickly rise through the sample cell, whereby entrapment of air bubbles within the sample cell is prevented thereby reducing air bubble noise;

(d) alternately pulsing at least two light sources having different wavelengths to produce a first pulsed light having a reference wavelength and a second pulsed light having a measuring wavelength;

(e) guiding the first and second pulsed lights to a fixed location adjacent an approximately first vertical side of the sample cell;

(f) transmitting the first and second pulsed lights across the sample cell such that the pulsed lights diffuse as they cross the sample cell, whereby the second pulsed light is absorbed by the species to a greater extent than the first pulsed light along optical paths traveled by the diffused pulsed lights across the species' flow path;

(g) reflecting portions of the first and second pulsed lights back to the fixed location with a concave mirror, the mirror being located adjacently to a second approximately vertical side of the sample cell, the approximately first vertical side and the second approximately vertical side being located on opposite sides of the sample cell, whereby in crossing the sample cell, the reflected second pulsed light is absorbed to a greater extent than the reflected first pulsed light along the optical paths traveled by the reflected lights to back to the fixed location;

(h) collecting portions of the reflected first and second pulsed lights at the fixed location, whereby reflecting diffused pulsed lights back to the fixed location increases the optical path lengths of the pulsed lights without increasing the sample cell's dead zone and also concentrates the diffused pulses so that substantial amounts of illumination which has been exposed to the species are available for collection at the fixed location;

(i) guiding portions of the reflected first and second pulsed lights away from the fixed location;

(j) converting the guided portions of the reflected first and second pulsed lights to a first and second electrical signal, the strength of the first signal being proportional to the illumination intensity of the portions of the reflected first pulsed signal guided away from the fixed location and said second signal being proportional to the illumination intensity of the portions of the reflected second pulsed signal guided away from the fixed location; and (k) comparing the logarithmic ratio of the signals to determine the absorption of the species.

2. The method in accordance with claim 1, wherein:
in step (a) the sample cell has two parallel flat sides, a first flat side and a second flat side, and the sample cell is aligned such that the two flat sides are approximately transverse to the optical paths of the pulsed lights;
in step (e) the first vertical side is the first flat side of the sample cell; and
in step (g) the second vertical side is the second flat side.

3. The method in accordance with claim 2 wherein in step (d) the light sources are light emitting diodes.

4. The method in accordance with claim 2 wherein in step (d) the light sources are laser diodes.

5. The method in accordance with claim 2 wherein in step (d) the light sources are a two-color light emitting diode, the colors being alternately pulsed.

6. The method in accordance with claim 3, wherein:
in step (d) the light emitting diodes are mounted together;
step (e) also includes guiding the pulsed lights to the fixed location on an optical guide having a plurality of branches, a first branch guiding the first and second pulsed lights between the fixed location and the light emitting diodes; and
step (i) also includes guiding the portions of the reflected first and second pulsed lights away from the fixed location with a second branch of the optical guide.

7. The method in accordance with claim 3, wherein:
in step (d) the light emitting diodes are mounted separately;
step (e) also includes guiding the pulsed lights to the fixed location on a three branch optical guide, the three branches are combined at one end of the optical guide to form a common end, the first and second pulsed lights being guided on a first and second branch of the guide the fixed location, the first and second branches extending between the fixed location and its associated separately mounted light emitting diode; and
step (i) also includes guiding the portions of the first and second reflected pulsed lights away from the fixed location on a third branch of the three branch optical guide.

8. The method in accordance with claim 7 wherein each branch has a plurality of optical fibers, the fibers from all the branches being combined in forming the common end such that branch fiber ends are randomly distributed across the common end.

9. The method in accordance with claim 7, wherein each branch has a plurality of optical fibers, the fibers being combined in forming the common end such that branch fiber ends from separate branches are evenly distributed across the common end.

10. The method in accordance with claim 7, wherein each branch has a plurality of optical fibers, each branch's fibers being a group of fibers wherein the group of fibers from one of the branches is located at the center of the common end with the groups of fibers from the remaining branches forming concentric circles about the center group of fibers.

11. The method in accordance with claim 2, wherein:
in step (g) the concave mirror is a spherical mirror and the fixed location is located at the center of curvature of the spherical mirror.

12. A dual-wavelength absorption detector adapted for continuous-flow detection, the absorption detector being functional to connect to a sample line having the capability of providing a continuous stream of material for sampling, the absorption detector comprising:

a detector-cell, the detector-cell includes a detector-cell body and a longitudinal sample cell;

the detector-cell body has four openings connecting to a central cavity within the body, the four openings including a top opening and a bottom opening located opposite each other and a third opening and a fourth opening located opposite each other and approximately transverse to the top and bottom openings;

a means for connecting the top opening to the sample line;

a means for connecting the bottom opening to the sample line wherein flow from the sample line is from bottom to top through the detector-cell;

the longitudinal sample cell has two flat parallel sides with the sample cell being located within the central cavity such that its longitudinal length is aligned approximately vertical, the sample cell including a bottom inlet and a top outlet which are functional to allow sample material from the sample line to flow through the sample cell, wherein bubbles are swept out of the sample cell by an upward flow of the sample material thereby preventing entrapment of bubbles within the sample cell and reducing the ability of the sample cell to cause bubble induced noise;

wherein the means for connecting the top opening to the sample line includes a means for removing the sample cell through the top opening for inspection, cleaning and replacement when the absorption detector's performance may have been reduced as a result contact with the sample material;

a means for alternately producing a first pulsed light having a reference wavelength and a second pulsed light having a measuring wavelength;

an optical guide, the optical guide having a plurality of branches, each branch of the optical guide having at least one optical fiber, fibers of the branches are combined at one end of the optical guide to form a common end which is connected to the detector-cell body's third opening such that fiber ends of the common end's fibers are located at a fixed location, the fixed location being adjacent to one of the parallel sides of the sample cell, the optical guide being functional for the guiding of light into and away from the detector-cell whereby the first and second pulsed lights are guided to at least one of the fiber ends where the pulsed lights diffuse upon leaving the guide to irradiate the sample material;

a concave mirror, the concave mirror is located within the fourth opening and on the opposite side of the sample cell from the fiber ends, the concave mirror being functional to reflect some of the pulsed lights back to the fiber ends whereby some of the reflected pulsed lights are collected by at least one of the fiber ends where they are guided away from the detector-cell;

a means for converting the guided first and second pulsed lights into a first electrical signal and a second electrical signal, the first electrical signal and the second electrical signal being respectively proportional to the intensity of the reflected first and second pulsed lights guided away from the detector-cell; and a means for comparing the first and second electrical signals such that the comparison represents a determination of the absorption of the sample material.

13. The absorption detector of claim 12 wherein the means for alternately producing the first and second pulsed lights includes at least two light emitting diodes which are alternately pulsed.

14. The absorption detector of claim 12 wherein the means for alternately producing the first and second pulsed lights include at least two laser diodes which are alternately pulsed.

15. The absorption detector of claim 12 wherein the means for alternately producing the first and second pulsed lights includes a two-color light emitting diode whereby the colors are alternately pulsed.

16. The absorption detector of claim 13 wherein the means for alternately producing the pulsed lights also includes pulsing the light emitting diodes such that the duty cycle of the diodes is less than ten per cent and drive currents of the diodes are increased above a value designated as the normal one hundred per cent duty cycle rating.

17. The absorption detector of claim 13 wherein:
the light emitting diodes are mounted together; and
the optical guide has at least one branch which guides pulsed lights to the detector-cell and at least one branch which guides reflected pulsed lights away from the detector-cell, whereby the pulsed lights produced by the diodes mounted together are guided by the same branch to the detector-cell.

18. The absorption detector of claim 13 wherein:
the light emitting diodes are mounted separately; and
the optical guide includes a separate branch for each separately mounted diode to guide pulsed light produced by its respective diode to the detector-cell and also includes at least one separate branch to guide the reflected pulsed lights away from the detector-cell.

19. The absorption detector of claim 12 wherein the concave mirror is a spherical mirror having as its center of curvature the fixed location.

20. The absorption detector of claim 12 wherein the sample cell has a tapered top, the tapered top having a round exterior top surface such that an o-ring may provide a pressure seal between the tapered top and the means for connecting the top opening to the sample line.

21. The absorption detector of claim 12 wherein the central cavity and the sample cell have dimensions which work in conjunction with each other to ensure a proper alignment of the sample cell with respect to the fixed location, the mirror and the means for connecting the top opening to the sample line.

22. The absorption detector of claim 12 wherein each branch of the optic guide has a plurality of optical fibers with the fibers being combined to form the common end.

23. The absorption detector of claim 22 wherein the fibers forming the common end have their fiber ends arranged in a random order.

24. The absorption detector of claim 22 wherein the fibers forming the common end have their fiber ends arranged such that fiber ends from each branch are evenly distributed across the common end.

25. The absorption detector of claim 22 wherein the fibers for each branch form a group of fibers at the common end and their fiber ends are arranged such that one group of fibers is located at the center of the common end and the remaining groups of fibers form concentric circles about the fiber ends of the group of fibers located at the center of the common end.

26. A dual-wavelength absorption detector adapted for continuous-flow detection, the absorption detector being functional to connect to a sample line having the capability of providing a continuous stream of material to be sampled, the material including at least one species for which absorption is to be determined, the detector having a configuration which substantially reduces bubble induced noise and at least doubles the sensitivity of the detector without increasing the detector's dead zone, the absorption detector comprising:

a means for alternately producing a first pulsed light having a reference wavelength and a second pulsed light having a measuring wavelength;

an approximately vertically aligned longitudinal sample cell having two parallel flat sides, a first flat side and a second flat side, the flat sides being opposite each other, the sample cell also having an opening at the bottom and an opening at the top, the bottom opening being functional to connect to the sample line such that the sample line provides the species as a continuous-flow of material into the sample cell, whereby the approximately vertically aligned sample cell allows bubbles to quickly pass through the cell to the top opening of the cell thereby reducing air bubble noise by preventing bubbles from being entrapped within the sample cell;

a three branched optical guide, each branch of the optical guide having a plurality of optical fibers, at one end of the optical guide, the fibers of each branch are combined to form a common end, the common end having fiber ends that are located at a fixed location adjacent to the sample cell, the sample cell being aligned with respect to the common end such that optical energy emerging from the fiber ends would be approximately transverse to the flat sides;

a first branch of the three branched optical guide, the first branch being functional for guiding the first pulsed light to the fixed location where the first pulsed light diffuses upon emerging from the first branch's fiber ends to irradiate the species;

a second branch of the three branched optical guide, the second branch being functional for guiding the second pulsed light to the fixed location where the second pulsed light diffuses upon emerging from second branches fiber ends to irradiate the species, whereby the second pulsed light is subjected to greater absorption along optical paths across the sample cell than the first pulsed light;

a concave mirror, the mirror being located adjacently to the second flat side of the sample cell, the concave mirror being functional to reflect some of the first and second pulsed lights back across the sample cell such that first and second reflected pulsed lights are concentrated at the fixed location with some of the first and second reflected pulsed lights striking the common end, whereby the second reflected pulsed light is subjected to a greater absorption along the optical paths back across the sample cell than the first reflected pulsed light;

a third branch of the three branched optical guide, the third branch being functional to guide the first and second reflected light pulses striking the third branch's fiber ends away from the fixed location, whereby reflecting the first and second light pulses from the concave mirror back across the sample cell to the common end at least doubled the optical path length thereby at least doubling the sensitivity of the detector;

a means for converting the guided first and second reflected pulsed lights into a first electrical signal and a second electrical signal, the first electrical signal and the second electrical signal being respectively proportional to the intensity of the reflected first and second pulsed lights guided by the third branch away from the fiber ends; and a means for comparing the first and second electrical signals such that the comparison represents a determination of the absorption of the species.

* * * * *